United States Patent [19]

Ciliberto et al.

[11] Patent Number: 5,681,723
[45] Date of Patent: Oct. 28, 1997

[54] MUTANT INTERLEUKIN 6 WITH IMPROVED BIOLOGICAL ACTIVITY OVER WILD INTERLEUKIN 6

[75] Inventors: Gennaro Ciliberto, Casalpalocco; Rocco Savino, Pomezia, both of Italy

[73] Assignee: Instituto di Ricerche di Biologia Molecolare P. Angelett S.P.A., Pomezia, Italy

[21] Appl. No.: 437,680

[22] Filed: May 5, 1995

Related U.S. Application Data

[63] Continuation-in-part of PCT/IT93/00114, Nov. 2, 1993.

[30] Foreign Application Priority Data

Nov. 6, 1992 [IT] Italy ................... RM92A0809

[51] Int. Cl.$^6$ ............ C12P 21/02; C07H 21/04; C07K 14/52; A61K 38/20
[52] U.S. Cl. ............ 435/69.52; 435/69.5; 435/69.51; 435/243; 435/252.3; 435/320.1; 530/351; 930/141; 930/142; 930/140; 536/23.5; 536/23.52; 424/85.2; 424/85.6
[58] Field of Search .................. 435/69.52, 69.51, 435/243, 252.3, 320.1; 530/351; 930/141, 142; 536/23.5, 23.52; 424/85.2, 85.6

[56] References Cited

U.S. PATENT DOCUMENTS 5,210,075  5/1993  Scholz et al. .................... 530/351

FOREIGN PATENT DOCUMENTS 331640  9/1989  European Pat. Off. .

OTHER PUBLICATIONS de Hon et al, *Cytokine* 7(5) 1995, p. 398–407.
Thier et al *J. Neurosci Res.* 40(6) 1995, pp. 826–835.
Skelly et al *J. Biotechnol* 34(1) 1994, pp. 79–86.
Savino et al, *PNAS* 90, 1993, pp. 4067–4071.
Fontaine et al *Eur. J. Biochem.* 211, 1993, pp. 749–755.
Li et al, *JBC* 268 (32) 1993, PP. 22377–22384.
Leebeek et al *JBC* 267(21) 1992, pp. 14832–14838.
Brakenhoff et al JBC 269(1) 994, pp. 86–93.
"Biochem. Biophys. Res. Communications" vol. 187, No. 1, Aug. 31, 1992, pp. 18–25.
"FEBS Letters" vol. 282, No. 2, pp. 265–267.
"Gene" vol. 104, No. 2, 1991, Amsterdam, pp. 227–234.

*Primary Examiner*—Garnette D. Draper
*Attorney, Agent, or Firm*—Birch, Stewart, Kolasch & Birch, LLP

[57] ABSTRACT

The present invention is drawn to mutant interleukin 6, which has the amino acid arginine in position 176, replacing serine in position 176 with wild-type interleukin 6. The mutant interleukin 6 of the present invention has greater biological activity than the wild-type protein. The present invention is further drawn to methods of making mutant interleukin 6, having arginine at position 176 and methods of using the same.

10 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 555 base pair
        ( B ) TYPE: nucleic acid
        ( C ) STRANDEDNESS: single
        ( D ) TOPOLOGY: linear (i i) MOLECULE TYPE: cDNA (i i i) HYPOTHETICAL: no (i v) ANTI-SENSE: no (v i) ORIGINAL SOURCE:
    (A) ORGANISM: Homo sapiens
    (B) DEVELOPMENTAL STAGE: Adult
    (C) CELL TYPE: monocyte (v i i) IMMEDIATE SOURCE:
    (A) LIBRARY: cDNA
    (B) CLONE: pB.B2.21

(x i) SEQUENCE DESCRIPTION: SEQ ID NO: 1:

```
CCA  GTA  CCC  CCA  GGA  GAA  GAT  TCC  AAA  GAT  GTA  GCC  GCC  CCA  CAC  AGA    48
Pro  Val  Pro  Pro  Gly  Glu  Asp  Ser  Lys  Asp  Val  Ala  Ala  Pro  His  Arg
 1              5                   10                            15

CAG  CCA  CTC  ACC  TCT  TCA  GAA  CGA  ATT  GAC  AAA  CAA  ATT  CGG  TAC  ATC    96
Gln  Pro  Leu  Thr  Ser  Ser  Glu  Arg  Ile  Asp  Lys  Gln  Ile  Arg  Tyr  Ile
              20                  25                       30

CTC  GAC  GGC  ATC  TCA  GCC  CTG  AGA  AAG  GAG  ACA  TGT  AAC  AAG  AGT  AAC   144
Leu  Asp  Gly  Ile  Ser  Ala  Leu  Arg  Lys  Glu  Thr  Cys  Asn  Lys  Ser  Asn
         35                       40                  45

ATG  TGT  GAA  AGC  AGC  AAA  GAG  GCA  CTG  GCA  GAA  AAC  AAC  CTG  AAC  CTT   192
Met  Cys  Glu  Ser  Ser  Lys  Glu  Ala  Leu  Ala  Glu  Asn  Asn  Leu  Asn  Leu
     50                  55                       60

CCA  AAG  ATG  GCT  GAA  AAA  GAT  GGA  TGC  TTC  CAA  TCT  GGA  TTC  AAT  GAG   240
Pro  Lys  Met  Ala  Glu  Lys  Asp  Gly  Cys  Phe  Gln  Ser  Gly  Phe  Asn  Glu
65                  70                       75                      80

GAG  ACT  TGC  CTG  GTG  AAA  ATC  ATC  ACT  GGT  CTT  TTG  GAG  TTT  GAG  GTA   288
Glu  Thr  Cys  Leu  Val  Lys  Ile  Ile  Thr  Gly  Leu  Leu  Glu  Phe  Glu  Val
                    85                       90                      95

TAC  CTA  GAG  TAC  CTC  CAG  AAC  AGA  TTT  GAG  AGT  AGT  GAG  GAA  CAA  GCC   336
Tyr  Leu  Glu  Tyr  Leu  Gln  Asn  Arg  Phe  Glu  Ser  Ser  Glu  Glu  Gln  Ala
                   100                      105                     110

AGA  GCT  GTC  CAG  ATG  AGT  ACA  AAA  GTC  CTG  ATC  CAG  TTC  CTG  CAG  AAA   384
Arg  Ala  Val  Gln  Met  Ser  Thr  Lys  Val  Leu  Ile  Gln  Phe  Leu  Gln  Lys
              115                      120                     125

AAG  GCA  AAG  AAT  CTA  GAT  GCA  ATA  ACC  ACC  CCT  GAC  CCA  ACC  ACA  AAT   432
Lys  Ala  Lys  Asn  Leu  Asp  Ala  Ile  Thr  Thr  Pro  Asp  Pro  Thr  Thr  Asn
         130                      135                     140

GCC  AGC  CTG  CTG  ACG  AAG  CTG  CAG  GCA  CAG  AAC  CAG  TGG  CTG  CAG  GAC   480
Ala  Ser  Leu  Leu  Thr  Lys  Leu  Gln  Ala  Gln  Asn  Gln  Trp  Leu  Gln  Asp
145                 150                      155                    160

ATG  ACA  ACT  CAT  CTC  ATT  CTG  CGG  AGC  TTT  AAG  GAG  TTC  CTG  CAG  TCC   528
Met  Thr  Thr  His  Leu  Ile  Leu  Arg  Ser  Phe  Lys  Glu  Phe  Leu  Gln  Ser
                   165                      170                     175

AGC  CTG  AGG  GCT  CTT  CGG  CAA  ATG  TAG                                      555
Ser  Leu  Arg  Ala  Leu  Arg  Gln  Met
              180
```

(2) INFORMATION FOR SEQ ID NO:2:

(i) SEQUENCE CHARACTERISTICS:
        (A) LENGTH: 60 base pair
        (B) TYPE: nucleic acid
        (C) STRANDEDNESS: single
        (D) TOPOLOGY: linear (i i) MOLECULE TYPE: oligonucleotide (i i i) HYPOTHETICAL: no (i v) ANTI-SENSE: yes (  v i i  ) IMMEDIATE SOURCE:
    ( A ) LIBRARY: DNA synthesizer ( x i ) SEQUENCE DESCRIPTION: SEQ ID NO: 2:

GGTGCTCGAG CTACATTTGC CGAAGAGCCC TCAGGCTNNN CTGCAGGAAC TCCTTAAAGC    60

MUTANT INTERLEUKIN 6 WITH IMPROVED BIOLOGICAL ACTIVITY OVER WILD INTERLEUKIN 6

This application is a continuation-in-part of PCT international application No. PCT/IT93/00114 which has an international filing date of Nov. 2, 1995, which designated the United States, the entire contents of which are hereby incorporated by reference.

DESCRIPTION

The present invention relates to mutant interleukin 6 having a biological activity on human cells that is significantly superior to that shown by wild interleukin 6.

As is known, interleukin 6 (hereinafter also indicated as IL-6) is a 184 amino acid polypeptide postulated to belong to the class of helical cytokines.

IL-6 is a multi-functional cytokine produced by a variety of cell types. It acts as a differentiation and growth factor on cells of various types, for example cells of the immune system, hepatocytes, kidney cells, hematopoietic stem cells, keratinocytes and neurons (Akira, S., Hirano, T. Taga, T. and Kishimoto, T. (1990) FASEB J. 4, 2861–2867; Hirano, T. (1991) International J. of Cell Cloning 9, 166–186; Hirano, T., Akira, S., Taga, T. and Kishimoto, T. (1990) Immunol. Today 11, 443–449; Van Snick, J., Cayphas, S., Vink, A., Uyttenhove C., Coulie, P. G. and Simpson, R. J. (1986) Proc. Natl. Acad. Sci. USA, 83, 9679–9683).

The three-dimensional model of human interleukin 6 (hIL-6) is based on the similarity of its hydrophobicity pattern with that of other cytokines and on the x-ray determination of the structure of proteins such as, for example, the growth hormone, interleukin 2, interleukin 4, interferon-beta and the Granulocyte Macrophage Colony Stimulating Factor. The resulting model, that is to say a bundle of four alpha-helices (A, B, C and D) with up-up-down-down topology connected by means of three loops, suggests that the nine carboxy-terminal amino acids could be folded into an alpha-helix or a non-helicoidal conformation interacting with residues in the A-B loop could be adopted. Experiments carried out during the present invention favour this second, non-helicoidal conformation. In this region others have already underlined the importance from a point of View of biological activity of the arginine in position 182 and methionine in position 184.

It has now been unexpectedly found that the mutant interleukin 6, subject of the present invention, with the amino acid arginine in position 176, in place of the amino acid serine as is the case in wild interleukin 6, shows a biological activity significantly higher than that of wild interleukin 6.

This is an extremely important result because of its effects in the field of medicine. The improved biological activity of mutant interleukin 6 according to the present invention makes it possible to use therapeutic doses between 2 and 4 times lower than those required when using wild interleukin 6 in the treatment of a number of serious diseases. In fact, interleukin 6 has important and promising applications in the treatment of breast cancer, leukemia, infectious diseases and diseases connected with disorders connected with bone marrow stem cells.

Subject of the present invention is therefore mutant interleukin 6, characterized in that it has, in position 176, the amino acid arginine instead of the amino acid serine as in wild interleukin 6, and in that it shows biological activity on human cells superior to that of wild interleukin 6. In particular, the biological activity of mutant interleukin 6 according to the present invention can be between three and five times higher than that of wild type interleukin 6.

The present invention also relates to a non-glycosylated polypeptide comprising the amino acid sequence of mutant interleukin 6 by substitution Ser 176 Arg.

The invention also relates to recombinant vectors comprising a DNA sequence coding for said polypeptide, and to transformed microorganisms containing it.

The invention also relates to a process for preparation of said non-glycosylated polypeptide by culture of said transformed microorganisms and subsequent recovery of the polypeptide.

Finally, the invention also relates to pharmaceutical compositions—for treatment of breast cancer, leukemia, infectious diseases connected with disorders of the bone marrow stem cells, and thrombocytopenia—containing, as active principle, mutant interleukin 6 with the amino acid arginine in position 176. Such compounds can be administered I.V.

The increased biological activity of mutant interleukin 6 according to the present invention is to be related to the increase affinity for the human interleukin 6 receptor, in the C-terminal region, due to the substitution, as residue 176, of serine with arginine.

The plasmid pBKS IL-6 Ser176Arg containing the nucleotidic sequence coding for mutant interleukin 6 according to the invention, non-glycosilated. This has been deposited in E. coli K12 with The National Collection of Industrial and Marine Bacteria Ltd., 28 St. Machar Dr., Aberdeen, Scotland UK AB2 1RY, on Feb. 11, 1992 under the terms of the Budapest Treaty and having access number NCIMB 40526.

Up to this point a general description has been given of the present invention. With the aid of the following examples, a more detailed description will now be given of embodiments thereof, to give a clearer understanding of its objects, characteristics, advantages and methods of application.

EXAMPLE 1

Preparation of Mutant Interleukin 6 by Substitution Ser176Arg

Ser176Arg substitution interleukin 6 was generated using the PCR strategy (as illustrated in Fontaine, V., Savino, R., Arcone, R., Brakenhoff, J. P. J., Content, J. and Ciliberto, G. (1992) Eur. J. Biochem; and represented in SEQ ID NO: 2 which corresponds, from nucleotide 11 to the end, to positions 506 to 555 (antisense strand) of IL-6 DNA (assuming +1 the first nucleotide of the first codon of the sequence coding for the mature polypeptide).

The nucleotidic sequence coding for the mature polypeptide and the amino acid sequence of the mature polypeptide are shown in the attached sequence listing as SEQ ID NO: 1

Purification of the amplified fragments, ligation in the pBKS IL-6 vector, screening and characterization of the mutant plasmids were carried out as described in the above mentioned work by Fontaine et al.

Some of the mutant cDNAs were subcloned into E. coli expression vector pT7.7 (Studier, F. W. and Moffatt, B. A. (1986) J. Mol. Biol. 189, 113–130); this was accomplished by excising the chosen cDNAs with SpeI and XhoI and ligating them in pT7.7 cut with XbaI (compatible with SpeI) and SalI (compatible with XhoI).

The mutant protein was expressed in two different ways, which will be indicated with a) and b) in the following.

a) In vitro transcription and translation

All mutant plasmids and pBKS IL-6 were linearized using Asp 718. Approximately one µg of DNA template was transcribed using the mCAP RNA capping kit (Stratagene, La Jolla, Calif.) according to the instructions furnished by the manufacturer. The transcribed RNAs were translated with rabbit reticolocytis lysate (Promega) for 90 minutes at 30° C. in presence of $^{35}$S-methionine (Amersham); 3 µl of the translation cocktail were analyzed by electrophoresis in 15% SDS-PAGE (as described in Fiorillo, M. T., Cabibbo, A., Iacopetti, P., Fattori E. and Ciliberto, G. (1992) Eur. J. 22, 2609–2615). After exposure, the bands corresponding to wild type and mutant hIL-6 were excised from the poly-acrylamide gel and their radioactivity was determined. The values were normalized taking into account the number of methionines present.

b) Production in E.coli

Wild type and mutant hIL-6 were expressed in *E. coli* and purified exactly as described in Arcone, R., Pucci, P., Zappatosta, F., Fontaine, V., Malorni, A., Marino, G. and Ciliberto, G. (1991) Eur. J. Biochem 198, 541–547; and in Fiorillo, M. T., Cabibbo, A., Iacopetti, P., Fattori, E. and Ciliberto, G. (1992) Eur. J. Immunol. 22, 2609–2615. The purity of the proteins was checked by electrophoresis in 15% SDS-PAGE and staining with Comassie Brilliant blue R-250. Their amount was quantified by Bio-Rad protein assay (Bio-Rad).

EXAMPLE 2

Biological Assays

The biological activity of the mutant of interest was determined first of all on cells of human origin. The activity of hIL-6 on human cells was assayed for its ability to enhance transcription from acute phase gene promoters in cells of hepatic origin (Morrone, G., Ciliberto, G., Oliviero, S., Arcone, R., Dente, L., Content, J. and Cortese, R. (1988) J. Biol. Chem. 263, 12554–12558). The mutant has therefore been tested as regards its ability to induce CAT (chloramphenicolacetyltransferase) activity from a fusion of C-reactive protein promotor (CRP) and CAT transfected into the human hepatoma cell line Hep3B (Arcone, R., Gualandi, G. and Ciliberto, G. (1988) Nucleic Acids Res., 16, 3195–3207; Fiorillo, M. T., Cabibbo, A., Iacopetti, P., Fattori, E., Ciliberto, G. (1992) Eur. J. Immunol. 22, 2609–2615). The results obtained using this system are of particular importance, as they depend on the efficiency of the interaction of cytokine with the homologous receptor system.

In particular, human Hep3B cells were transfected with 45–50 µg of the plasmid -219 CRP-CAT containing the IL-6 responsive element of the CRP promoter gene. Transfection was performed in 20 ml of Dulbecco's Modified Eagle Medium (DMEM, Gibco) supplemented with serum 10% fetal calf and 2 mM L-glutamine using the calcium phosphate precipitation technique (Graham, I. F. L. and Van der Eb, A. J. (1973) Virology 52, 456–467). After 16–18 hours, precipitates were removed, cells were trypsinized, pooled, counted and plated in equal number ($10^5$ to $3 \times 10^5$) in 5 cm diameter petri dishes; 7–9 hours after plating, cells were induced for 36–40 hours with increasing amounts of mutant or wild-type hIL-6. Cell extracts and CAT assays were performed as described by Gorman, C. (1985) in "DNA cloning; a practical approach" (Glover, M. D., ed.) pages 143–190, IRL Press, Oxford.

The assay was carried out in duplicate (in triplicate in case of wild type hIL-6) with serial dilutions of two to four independent preparations of mutant. The activity of the mutant, expressed as a percent of wild type hIL-6, was calculated as the ratio between the amount of wild type hIL-6 and the amount of the mutant under examination necessary to give half maximal stimulation.

Giving the biological activity of wild type interleukin 6 to be 100% in this assay, the biological activity of mutant interleukin 6 according to the present invention, with Ser176Arg (S176R) substitution, shows, as reported in the following table 1, a value of 370±90%, which is thus a value equal to three to four times that of the wild type protein.

TABLE 1

| Comparison of receptor binding and biological activity | | |
|---|---|---|
| Mutation | Biological activity (% of wt hIL-6) | hIL-6R binding (% of wt hIL-6) |
| S176R | 370 ± 90% | 320 ± 87% |

Affinity for the soluble hIL-6 receptor of mutant hIL-6 produced in *E. coli* compared to the observed biological activity.

Mutant interleukin 6 according to the present invention has also been tested using the classical HGF (Hybridoma Growth Factor) assay for its ability to stimulate growth of the hIL-6 dependent murine hybridoma cell line 7TD1 (Van Snick, J., Cayphas, S., Vink, A., Uyttenhove, C., Coulie, P. G. and Simpson, R. J. (1986) Proc. Natl. Acad. Sci. USA, 83, 9679–9683). The assay was performed taking into account the indications of Fiorillo, M. T., Cabibbo, A., Iacopetti, P., Fattori, E. and Ciliberto, G. (1992) Eur. J. Immunol. 22, 2609–2615. In this case also a significant increase in biological activity has been seen in the mutant interleukin 6 with respect to the wild type.

We claim:

1. Mutant interleukin 6, containing, in position 176, the amino acid arginine, in place of the amino acid serine as in wild-type interleukin 6.

2. A non-glycosylated polypeptide comprising the amino acid sequence of mutant interleukin 6 of claim 1.

3. A recombinant vector comprising a DNA sequence coding for said polypeptide of claim 2.

4. The recombinant vector of claim 3, comprising the plasmid pBKS IL-6 Ser176Arg deposited with The National Collection of Industrial and Marine Bacteria Ltd. under accession number NCIMB 40526.

5. A transformed microorganism, containing said recombinant vector of claim 3.

6. The transformed microorganism of claim 5, wherein said microorganism is *E. coli*.

7. The transformed microorganism of claim 5 wherein said microorganism is *E. coli* K12.

8. A process for the preparation of a non-glycosylated mutant interleukin 6 having arginine in position 176 comprising culturing a transformed microorganism according to claim 5 and subsequently recovering said non-glycosylated mutant interleukin 6.

9. A pharmaceutical composition comprising the mutant interleukin 6 of claim 1, together with a pharmaceutically acceptable carrier.

10. A method of treating thrombocytopenia comprising administering to a patient in need thereof an effective amount of a compound of claim 2.

* * * * *

UNITED STATES PATENT AND TRADEMARK OFFICE
CERTIFICATE OF CORRECTION

PATENT NO.   : 5,681,723
DATED        : Oct. 28, 1997
INVENTOR(S)  : Ciliberto et al.

It is certified that error appears in the above-identified patent and that said Letters Patent is hereby corrected as shown below:

Please correct the cover page of the patent as follows:

Category [73]: Replace "Instituto di Ricerche di Biologia Molecolare P. Angelett S.P.A." with --Istituto di Ricerche di Biologia Molecolare P. Angeletti S.p.A.--

Signed and Sealed this

Sixteenth Day of March, 1999

Attest:

Q. TODD DICKINSON

*Attesting Officer*          *Acting Commissioner of Patents and Trademarks*